US00PP10222P

United States Patent [19]

Evison

[11] Patent Number: Plant 10,222

[45] Date of Patent: Feb. 3, 1998

[54] CLEMATIS PLANT NAMED 'EVIONE'

[75] Inventor: Raymond J. Evison, Guernsey, Great Britain

[73] Assignee: Poulsen Roser International S.A.R.L., Gaillac, France

[21] Appl. No.: 627,506

[22] Filed: Apr. 5, 1996

[51] Int. Cl.[6] ..... A01H 5/00

[52] U.S. Cl. ..... Plt./54.1

[58] Field of Search ..... Plt./54.1

[56] References Cited

PUBLICATIONS

GTITM UPOVROM Citation for *Clematis* 'Evione' dated Oct. 28, 1993.

*Primary Examiner*—James R. Feyrer

*Attorney, Agent, or Firm*—Foley & Lardner

[57] ABSTRACT

A clematis with purple tepals having a red/purple central stripe distinguished by yellow anthers and a free flowering habit.

6 Drawing Sheets

BACKGROUND OF THE INVENTION

The present invention relates to a new and distinct variety of purple/red striped clematis plant known by the cultivar name 'Evione', and formerly known under the breeder's reference name of Sugar Candy. It was discovered as a chance seedling of unknown parentage in a cultivated area at St. Sampsons' Parish, Guernsey, Channel Islands, Great Britain.

There are several striped clematis cultivars in various shades of pink, violet, and purple. Of these cultivars, the nearest to 'Evione' is 'Bee's Jubilee.' The following unique combination of characteristics that are outstanding in 'Evione' have been repeatedly observed in asexually propagated progeny and distinguish it from 'Bee's Jubilee' and from all other varieties of which I am aware: (1) yellow anthers (anthers of most other clematis varieties are red or reddish-brown); and (2) a free flowering habit.

This variety has not been observed under all possible environmental conditions. The phenotype of clematis plants can vary significantly with variations in environment such as temperature, light intensity, day length, and soil. The following observations, measurements and comparisons describe plants grown under growing conditions which are similar to those generally used in commercial practice.

Asexual reproduction of this new variety was by vegetative cuttings as performed at Guernsey, Channel Islands, Great Britain, and showed that the foregoing characteristics are established and transmitted through succeeding asexual propagations.

BRIEF DESCRIPTION OF THE PHOTOGRAPHS

The accompanying photographs show typical specimens of the foliage and flowers of this new variety, depicted in color as nearly true as it is reasonably possible to make the same in a color photograph of this character. The photographs were taken in June 1994 at a nursery located in St. Sampsons' Parish, Guernsey, Channel Islands, Great Britain.

Sheet 1 is a view of a cluster of flowers on a plant of 'Evione.'

Sheet 2 is a view of a single flower of 'Evione' that has been flattened to show the tepal arrangement.

Sheet 3 is a side view of an isolated flower of 'Evione' to more clearly show the flower center, including the yellow anthers of the variety.

Sheet 4 is a view of flower buds of 'Evione.'

Sheet 5 is a view of a leaf of 'Evione.'

Sheet 6 shows a flower of 'Bee's Jubilee' exhibiting reddish-brown anthers.

The following is a detailed description of my new clematis cultivar grown under glass at a nursery located in St. Sampsons' Parish, Guernsey, Channel Islands, Great Britain, throughout the flowering period. The color descriptions used herein employ terminology in accordance with The Royal Horticultural Society (London) Colour Chart, except where ordinary dictionary significance of color is indicated.

Classification:

*Botanical.*—Clematis cv. Evione.

*Commercial.*—Clematis.

Parentage:

*Seed parent.*—Unknown.

*Pollen parent.*—Unknown.

Plant:

*Form.*—Upright climbing or spreading.

*Growth.*—Medium growth. Height attained (first season): About 2.5 m.

*Foliage.*—Deciduous; compound — tri-foliate, sometimes simple. Size: Medium. Quantity: Average. Color: New Foliage: Upper Side: Light Green (R.H.S. 137D). Underside: Light Green (R.H.S. 137D). Old Foliage: Upper Side: Green (R.H.S. 137A). Underside: Light green (R.H.S. 137D). Shape: Normally three lanceolate leaflets in pinnate form. Lower leaves sometimes simple. Texture: Upper Side: Glabrous. Underside: Ribbed. Edge: Normal. Serration: None. Petiole Color: Top Surface: Green. Underside: Green. Stipules: None. Internodes: Shape: Cylindrical. Length: About 12 cm to about 17 cm. Resistance to disease: Subject to any disease that normally affects clematis, but less prone to mildew than some clematis.

*Wood.*—New shoots: Color: Light green. Bark: Smooth; light white hairs. Old wood: Color: Light brown. Bark: Rough.

*Hardiness.*—Zone 4–9.

Flower:

*Blooming habit.*—Recurrent.

*Bud.*—Size: About 4 cm to about 5 cm. Form: Ovate. Color: Green/grey, occasional red veins. Sepals: None (tepals only). Peduncle: Length: About 11 cm to about 15 cm. Aspect: Vertical. Strength: Erect. Color: Green (R.H.S. 143C). Bracts: None.

*Bloom.*—Average size when fully open: About 13 to about 18 cm. Borne: Singly. Form: Tepals opening to become flat. Number of tepals: Normally 6, sometimes 8. Color: Outer tepals: Top surface: Purple (R.H.S. 76A) with red/purple central bar (R.H.S. 71A). Undersurface: Purple (R.H.S. 76B). Base of tepals: Light purple with red stripe. General tonality from a distance: Pale purple. Color change: As bloom ages, all color lightens.

*Tepals.*—Texture: Medium. Appearance: Top surface: Satiny. Under surface: Satiny. Form: Obovate. Arrangement: Regularly arranged. Petaloids in center: None. Persistence: Tepals persist. Fragrance: None. Lasting quality: Two weeks on plant, only a few days as a cut flower.

Reproductive organs:

*Stamens, filaments and anthers.*—Arrangement: Regularly arranged. Color: Stamens: White base, yellow tip. Filaments: White base becoming purple at joint with anther. Anthers: Yellow.

*Pollen.*—Color: Light brown.

*Styles.*—Bunched, even, average length.

*Stigmas.*—Color: White.

*Hips.*—None (but produces seed heads).

I claim:

1. A new and distinct variety of clematis plant named 'Evione' as herein shown and described.

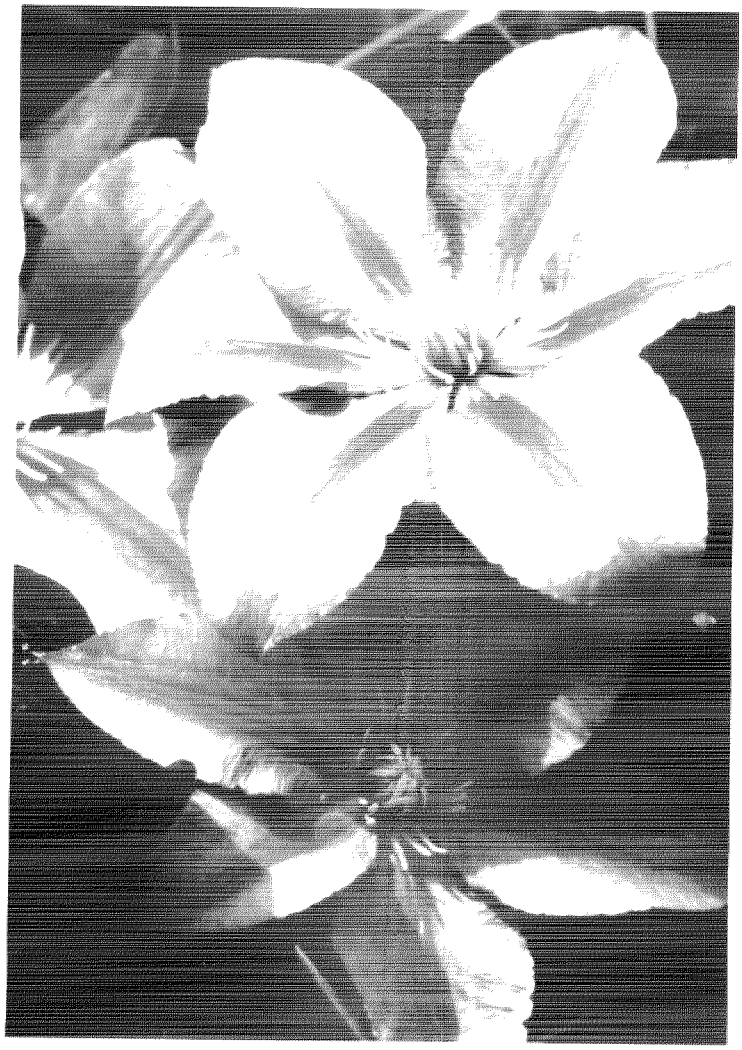

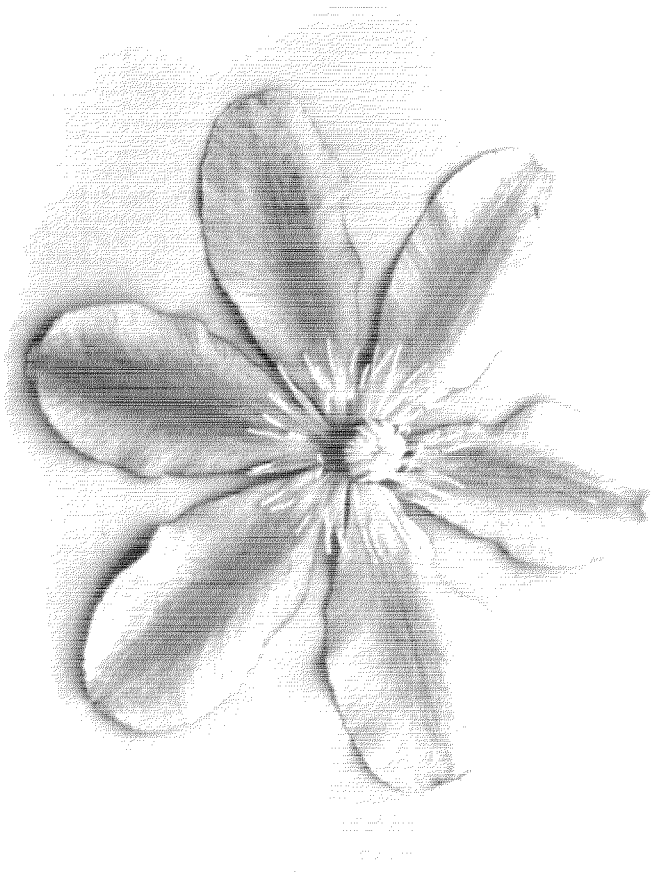

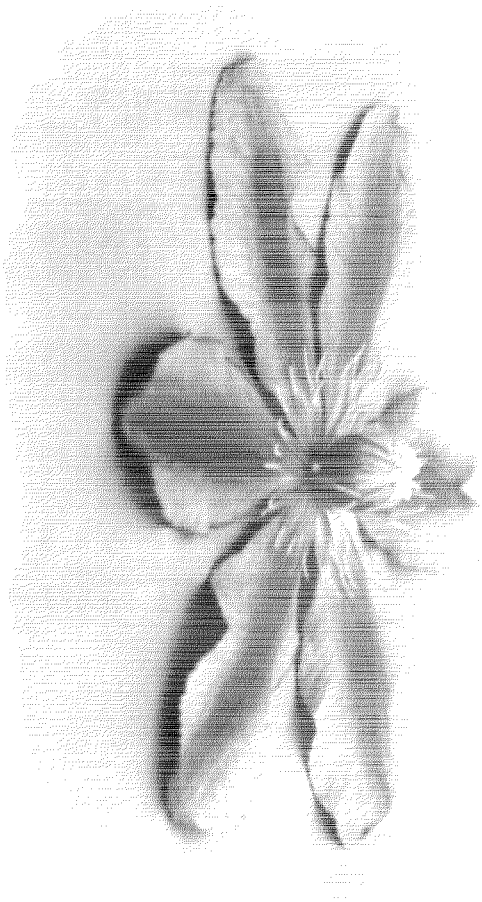

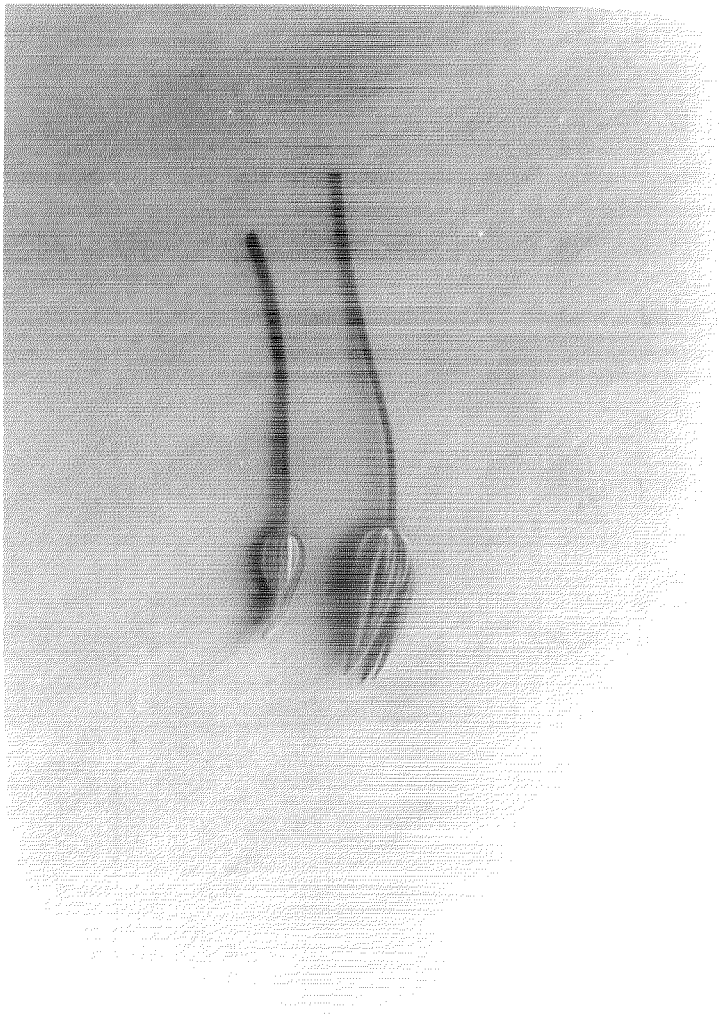

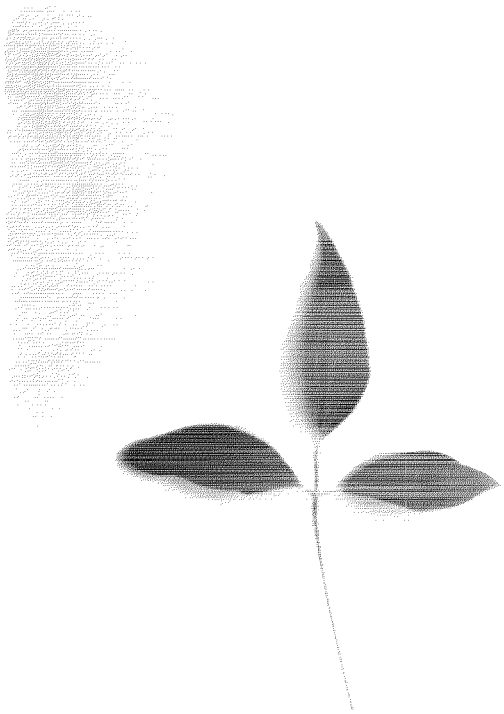

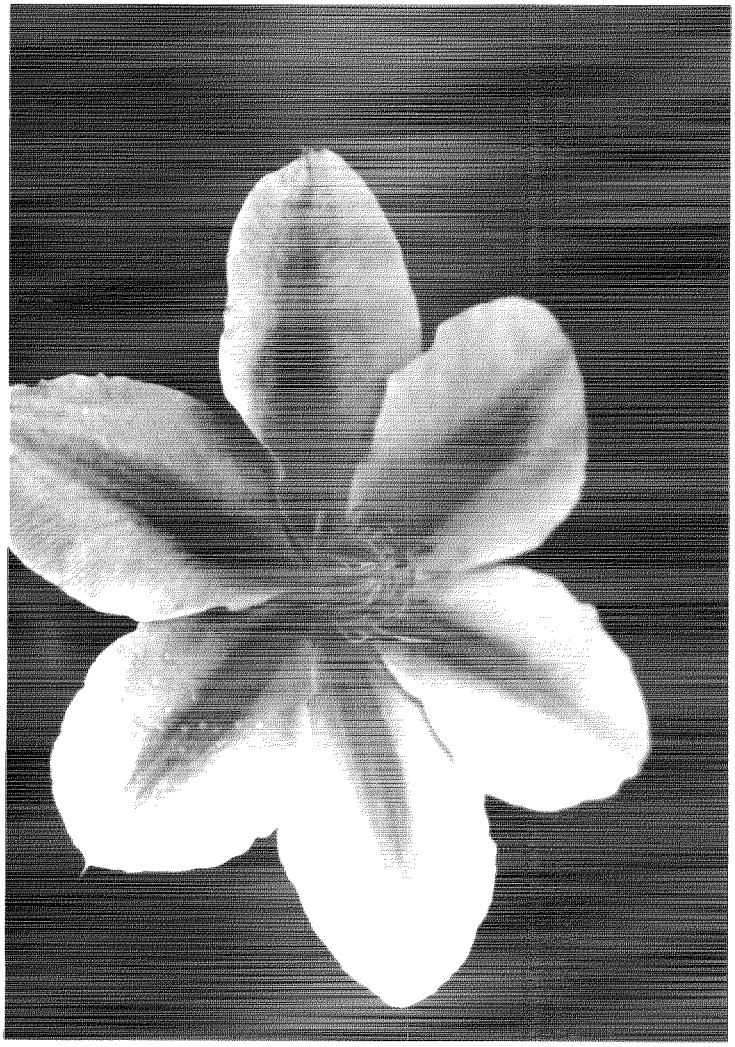

* * * * *